US009494573B2

(12) United States Patent
Anant et al.

(10) Patent No.: US 9,494,573 B2
(45) Date of Patent: Nov. 15, 2016

(54) IN VITRO TUMOR IN DISH KIT AND METHOD

(71) Applicant: University of Kansas, Lawrence, KS (US)

(72) Inventors: Shrikant Anant, Shawnee, KS (US); Prabhu Ramamoorthy, Lawrence, KS (US); Satish Ramalingam, Tamil Nadu (IN); Gurusingham Sitta Sittampalam, Fishers, IN (US)

(73) Assignee: University of Kansas, Lawrence, KS (US)

( * ) Notice: Subject to any disclaimer, the term of this patent is extended or adjusted under 35 U.S.C. 154(b) by 90 days.

(21) Appl. No.: 13/897,678

(22) Filed: May 20, 2013

(65) Prior Publication Data

US 2013/0316392 A1 Nov. 28, 2013

Related U.S. Application Data

(60) Provisional application No. 61/688,937, filed on May 24, 2012, provisional application No. 61/712,974, filed on Oct. 12, 2012.

(51) Int. Cl.
*C12Q 1/18* (2006.01)
*C12N 5/09* (2010.01)
*G01N 33/50* (2006.01)

(52) U.S. Cl.
CPC ......... *G01N 33/5011* (2013.01); *C12N 5/0693* (2013.01); *C12N 2502/1323* (2013.01); *C12N 2502/28* (2013.01); *C12N 2503/02* (2013.01)

(58) Field of Classification Search
CPC ............ C12N 2502/28; C12N 5/0693; C12N 2503/02
See application file for complete search history.

(56) References Cited

U.S. PATENT DOCUMENTS

| | | | |
|---|---|---|---|
| 2007/0087435 A1* | 4/2007 | Skorecki et al. ............. | 435/366 |
| 2008/0070303 A1* | 3/2008 | West et al. .................... | 435/377 |
| 2008/0248005 A1 | 10/2008 | Phan ............................. | 424/93.7 |
| 2010/0112691 A1* | 5/2010 | Green et al. .................. | 435/377 |
| 2010/0136114 A1* | 6/2010 | Mao ............................. | 424/486 |
| 2011/0305672 A1 | 12/2011 | Dalton et al. ................ | 424/93.7 |

FOREIGN PATENT DOCUMENTS

WO    WO 2009/124997 A1    10/2009

OTHER PUBLICATIONS

Dufau et al. "Multicellular Tumor Spheroid Model to Evaluate Spatio-Temporal Dynamics Effect of the Chemotherapeutics: Application to the Gemcitabine/CHK1 Inhibitor Combination in Pancreatic Center" BioMed Central Cancer 2012 12:15.
Frongia et al. "3D Imaging of the Response to CDC25 Inhibition in Multicellular Spheroids" Cancer Biology and Therapy 2009 8(23):2228-2234.
Hirschhaeuser et al. "Multicellular Tumor Spheroids: An Underestimated Tool is Catching Up Again" Journal of Biotechnology 2010.doi:10.1016/j.jbiotec.2010.01.012.
(Continued)

*Primary Examiner* — Sharmila G. Landau
*Assistant Examiner* — Sheridan Macauley
(74) *Attorney, Agent, or Firm* — Licata & Tyrrell P.C.

(57) ABSTRACT

This invention is a method and kit for preparing a Tumor in Dish model for use in screening anti-cancer agents and analyzing cancer growth and development.

5 Claims, 13 Drawing Sheets

(56) References Cited

OTHER PUBLICATIONS

Ho et al. "Development of Multicellular Tumor Spheroid (MCTS) Culture from Breast Cancer Cell and a High Throughput Screening Method Using the MTT Assay" PLoS ONE 7(9):e44640.doi:10.1371/journal.pone.0044640, 2012.
Kunz-Schughart et al. "The Use of 3-D Cultures for High-Throughput Screening: The Multicellular Spheroid Model" Journal of Biomolecular Screening 2004 9(4).doi:10.1077/1087057104265040.
Akimoto et al. "Temperature-Induced Intracellular Uptake of Thermoresponsive Polymeric Micelles" Biomacromolecules 2009 10(6):1331-1336 [Abstract only].
Brisson et al. "Establishment of Human Tumoral Ependymal Cell Lines and Coculture with Tubular-Like Human Endothelial Cells" International Journal of Oncology 2002 21(4):775 [Abstract only].
International Search Report from PCT/US2013/041757, Nov. 22, 2013, PCT.

* cited by examiner

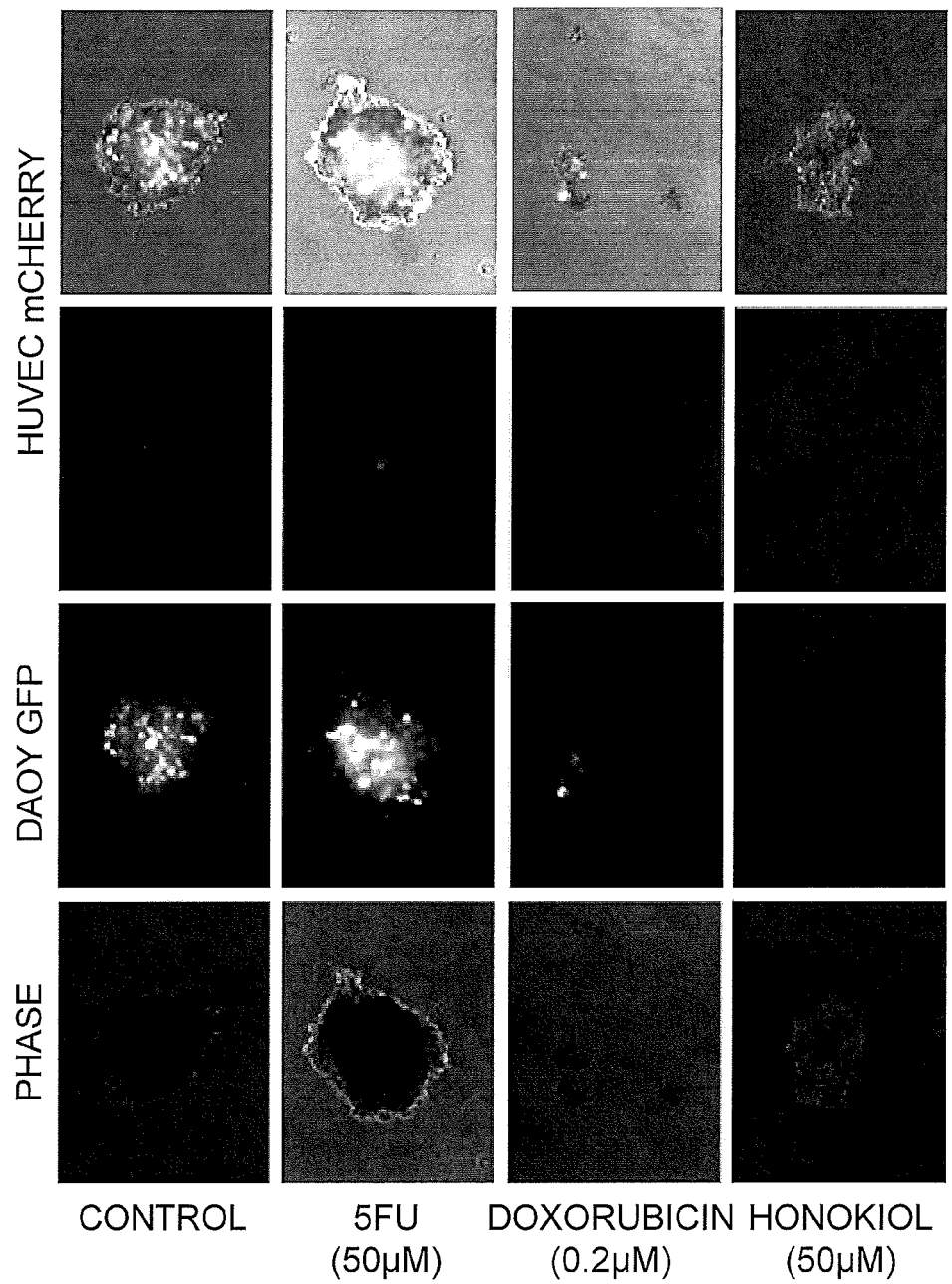

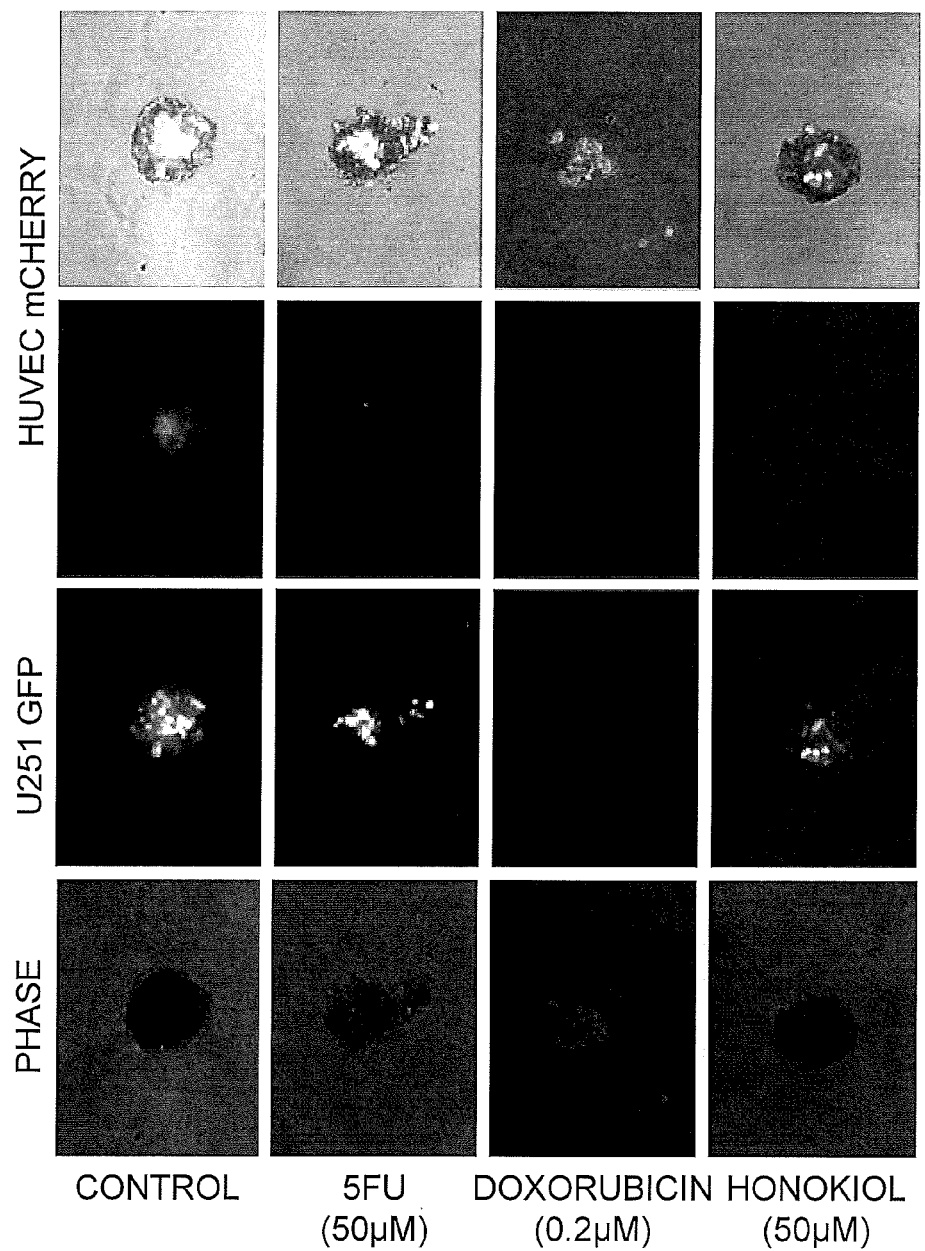

IN VITRO TUMOR IN DISH KIT AND METHOD

INTRODUCTION

This application claims the benefit of U.S. Provisional Application Nos. 61/688,937 filed May 24, 2012 and 61/712,974 filed Oct. 12, 2012, whose contents are incorporated herein by reference in their entireties.

BACKGROUND OF THE INVENTION

Pharmacokinetics is the study of the fate of pharmaceuticals and other biologically active compounds from the time they are introduced into the body until they are eliminated. Pharmacokinetics provides a rational means of approaching the metabolism of a compound in a biological system. One of the fundamental challenges researchers face in drug, environmental, nutritional, consumer product safety, and toxicology studies is the extrapolation of metabolic data and risk assessment from in vitro cell culture assays to animals.

To develop treatment options for patients diagnosed with tumors that are non-responsive or respond poorly to treatment with a particular anti-cancer agent, there is a need for reliable robust cell lines and models that are suitable for evaluating various treatment modalities. In particular, there is a need for cell lines and models that enable the development of effective therapies for the treatment of cancer that is non-responsive or responds poorly to current treatment regimes. Furthermore, there is a great need for cell lines and models for screening drug candidates for the treatment of cancer.

The failure rate for drugs in phase clinical trials has been rising. More than 50% of these failures are due to insufficient efficacy, and almost 20% are due to toxicity. Despite identification of a vast number of anti-cancer agents against cancer cell lines in artificial cell-based two-dimensional culture system, treatment of cancer remains challenging. Therefore, developing effective model systems that better represent the in vivo tumor is imperative.

SUMMARY OF THE INVENTION

This invention is a kit for a Tumor in Dish model. The kit is composed of culture medium or culture medium ingredients, isolated human umbilical vein endothelial cells, isolated human lymphatic endothelial cells, isolated human fibroblast cells, and isolated human epithelial cells. In some embodiments, the kit further includes isolated cancer cells and/or an ultra low attachment culture vessel.

A method for preparing a Tumor in Dish model is also provided, which includes (a) combining isolated human umbilical vein endothelial cells, isolated human lymphatic endothelial cells, isolated human fibroblast cells, isolated human epithelial cells and isolated cancer cells; and (b) culturing the combination of cells in culture medium for a time sufficient to form a tumor thereby preparing a Tumor in Dish model. In one embodiment, step (a) is carried out by (i) combining isolated human umbilical vein endothelial cells, isolated human lymphatic endothelial cells, isolated human fibroblast cells and isolated human epithelial cells; (ii) culturing the combination of cells of (i); (iii) adding isolated cancer cells to the cultured cells of (ii). In other embodiments, the method is carried out in an ultra low attachment culture vessel. In further embodiments, the method includes the steps of (c) adding a test compound; and (d) determining whether the test compound inhibits, attenuates, prevents or reduces tumor growth, proliferation, size or metastasis.

In certain embodiments, the growth medium of the kit and method include Microvascular Endothelial Cell Growth Medium; Airway Epithelial Basal Medium; Dulbecco's Modified Eagle's Medium, Mammary Epithelial Cell Basal Medium, or Roswell Park Memorial Institute 1640 Medium; Fibroblast Growth Medium; Hydrocortisone; Fibroblast growth factor 6; Insulin-Like Growth Factor-I; Ascorbic Acid; Vascular Endothelial Growth Factor; Human Epidermal Growth Factor; Heparin; Fetal Bovine Serum; Antibiotics; L-Alanyl-L-Glutamine; Extract P; Plasma Protein Fraction; Epinephrine; Transferrin; Thyroxine 3; Insulin; and B27 supplement.

BRIEF DESCRIPTION OF THE DRAWINGS

FIG. 3H is a graphical representation of the percentage decrease in GFP cells.

FIG. 6 demonstrates that the TiD model can be used for various types of cancers including medulloblastoma (FIG. 6A) and glioblastoma (FIG. 6B).

DETAILED DESCRIPTION OF THE INVENTION

Figure 1:
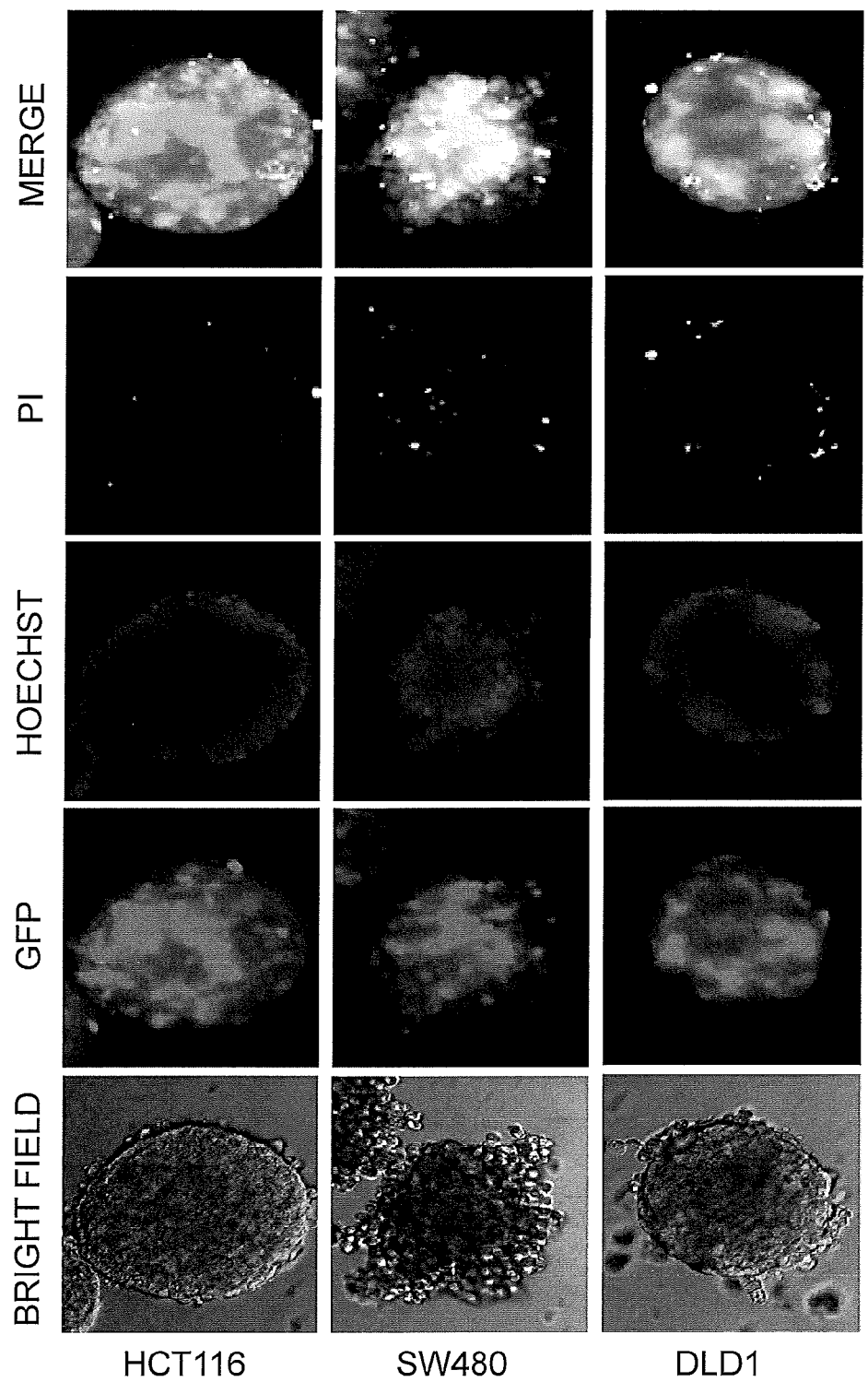
FIG. 1 shows live-dead staining of the Tumor in Dish (TiD) model. This analysis shows that most of the cells in the TiD are live cells, which are stained with Hoescht stain. In addition, colon cancer cells are evident by green fluorescent protein (GFP) fluorescence, while very few propidium iodide (PI)-stained dead cells were observed.

A novel medium and in vitro tumor model, which employs a unique combination of cell types and number of normal cells, have now been developed. Therefore, this invention provides a kit and method for preparing a Tumor in Dish model. In accordance with this invention, cancer cells self-assemble in a three dimensional spheroid culture along with normal epithelial, fibroblast, and endothelial cells, which create the in vivo-like cellular microenvironment. The tumor spheroids are grown in cell culture medium without additional extracellular matrix components. This is unique as it mimics real human tumors. This model provides cell-cell contact, architecture, and influence of different types of cells in the tumor microenvironment. Furthermore, it has been observed that gene expression in 3D is much closer to clinical expression profiles than those seen in 2D.

The Tumor in Dish model of this invention provides an easy, reproducible and more reliable therapy testing system with the potential to predict clinical efficacy. Therefore, the kit and method of this invention can be used for high throughput screening of drugs in a short period of time with limited amount of drug, as well as in methods for analyzing the effects of hypoxia, core necrosis, therapy resistance, angiogenesis, invasion and metastasis in the tumor microenvironment.

A kit of this invention includes normal cells, which create the in vivo-like cellular microenvironment, as well as culture medium or culture medium ingredients for supporting the growth of tumor spheroids. In addition, the kit can include one or more primary cancer cells or cancer cell lines. The cells of the kit can be provided in lyophilized form. Moreover, the cells can be provided as individual cell types or as mixtures of cell types in one or more containers. The kits can also contain, or be packaged with other items, such as a culture vessel and/or instructions for use.

Cells of the kit and method of this invention include isolated human umbilical vein endothelial cells, isolated human lymphatic endothelial cells, isolated human fibroblast cells, isolated human epithelial cells and isolated cancer or tumor cells. The cells are isolated in the sense that they are not present in their natural environment or organ. Isolated human cells can be obtained commercially, for example from ATCC (Manassas, Va.), Cell Systems, Inc. (Kirkland, Wash.), Clonetics Corporation (San Diego, Calif.), BioWhittaker (Walkersville, Md.), or Cascade Biologicals (Portland, Oreg.). Alternatively, cells can be isolated directly from samples of tissue obtained via biopsy, autopsy, donation or other surgical or medical procedure.

The isolation of cells is typically carried out by harvesting the tissue of interest and cutting the tissue into small pieces (e.g., 0.5×0.5 cm) using sterile surgical instruments. The small pieces are typically washed with sterile saline solution supplemented with antibiotics, and then optionally treated with an enzymatic solution (e.g., collagenase or trypsin solutions, each available commercially, for example, from GIBCO/LTI, Gaithersburg, Md.) to promote dissociation of cells from the tissue matrix. The mixture of dissociated cells and matrix molecules are then washed with a suitable physiological saline or tissue culture medium (e.g., Dulbecco's Phosphate Buffered Saline without calcium and magnesium). Between washes, the cells are centrifuged (e.g., at 200×g) and then resuspended in serum-free tissue culture medium. Aliquots are counted using an electronic cell counter (such as a Coulter Counter). Alternatively, the cells can be counted manually using a hemocytometer. Once in single cell form, the cells can be isolated by positive and/or negative selection, e.g., on particular growth media or by FACS.

Human Umbilical Vein Endothelial Cells (HUVEC) can be isolated from human umbilical vein. These cells can be identified by the expression of the well-characterized endothelial markers CD31, VE cadherin, multimerin, the KDR vascular endothelial cell receptor, and von Willebrand factor, as well as endothelial differentiation sphingolipid G-protein coupled receptor (EDG-1), melanoma adhesion receptor (MCAM), endothelin-1, ICAM2, protein C receptor, thymosin-β4, and plasminogen activator inhibitor type I (Ho, et al. (2002) Physiol. Genomics 13:249-62). While HUVEC are expressly disclosed herein, it is contemplated that other endothelial cells, including those from coronary artery (HCAEC), aorta (HAEC), portal artery (HPAEC), umbilical artery (HUAEC), iliac artery (HIAEC) and the pulmonary microcirculation (HMVEC) could be used in accordance with this invention.

Human lymphatic endothelial cells can be isolated from primary dermal microvascular endothelial cells. Markers of lymphatic endothelium include LYVE-1 (Jackson, et al. (1999) Trends Cardiovasc. Med. 13(1):1-7), Prox1 (Wigle, et al. (2002) EMBO J. 21:1505-13), VEGFR-3 (Veikkola, et al. (2001) EMBO J. 20:1223-31) and podoplanin (Breiteneder-Geleff, et al. (1999) Am. J. Pathol. 154:385-94).

Human fibroblast cells are cells that synthesize the extracellular matrix and collagen. Fibroblasts have a branched cytoplasm surrounding an elliptical, speckled nucleus having 1 or 2 nucleoli and are the most common cells of the connective tissue. Therefore, fibroblasts can be isolated from various sources include, but not limited to, skin and lung. Markers of fibroblast cells include Thy-(Saalbach, et al. (1998) Arch. Dematol. Res. 290:360-6), and 1B10 (Simonart, et al. (2002) J. Cutan. Pathol. 29:72-8).

Human epithelial cells can be derived from any epithelial tissue including, but not limited to intestinal, skin, olfactory, or respiratory epithelium. The intermediate filament proteins in the cytokeratin group (e.g., cytokeratin 4, 5, 6, 8, 10, 13, and 18) are almost exclusively found in epithelial cells, and therefore, these proteins are of use as epithelial cell markers.

Culture medium or culture medium ingredients are also provided by the kit and method of this invention. The term "ingredient" refers to any compound, whether of chemical or biological origin, that can be used in cell culture media to maintain or promote the growth of proliferation of cells. The terms "component," "nutrient" and "ingredient" can be used interchangeably and are all meant to refer to such compounds. The ingredients of the culture medium of this invention, and examples of commercial sources of the same, are set forth in Table 1. Other ingredients that promote or maintain cultivation of cells ex vivo can be selected by those of skill in the art, in accordance with the particular need. However, in certain embodiments, the kit and method of this invention do not include the addition of isolated extracellular matrix components such as type I collagen, type IV collagen, fibronectin, glycosaminoglycans or laminin.

TABLE 1

| Component | Source |
| --- | --- |
| EGM MV Microvascular Endothelial Cell Growth Medium[1] | Lonza/Clonetics Inc. (Basel, Switzerland) |
| Airway Epithelial Basal Medium[2] | ATCC (Manassas, VA) |
| Dulbecco's Modified Eagle's Medium (DMEM)[3] or | Life Technologies (Grand Island, NY) |
| Mammary Epithelial Cell Basal Medium (MEBM)[4] or | Lonza/Clonetics Inc.; Genlantis (San Diego, CA) |
| Roswell Park Memorial Institute (RPMI) 1640 Medium[5] | Life Technologies |
| Fibroblast Growth Medium[6] | Lonza/Clonetics Inc.; Genlantis (San Diego, CA) |
| Hydrocortisone[7] | Sigma-Aldrich |
| Fibroblast growth factor 6 (FGF)[8] | Sigma-Aldrich |
| Vascular endothelial growth factor (VEGF)[9] | BD Biosciences (San Jose, CA) |
| Human recombinant analog of insulin-like growth factor-I with the substitution of Arg for Glu at position 3 (R3-IGF-1)[10] | ABCAM (Cambridge, MA) Cell Sciences, Inc. (Canton, MA) |
| Ascorbic Acid[11] | Sigma-Aldrich |
| Human epidermal growth factor (hEGF)[12] | BD Biosciences |
| Heparin calcium salt[13] | MP Biomedicals (Solon, OH) |
| Fetal bovine serum (FBS)[14] | Sigma-Aldrich |

TABLE 1-continued

| Component | Source |
|---|---|
| Penicillin/Streptomycin (P/S)[15] | ScienCell Research Labs (Carslbad, CA); ATCC |
| L-Alanyl-L-Glutamine[16] | Ajinomoto (Raleigh, NC) Sigma-Aldrich |
| Extract P[17] | Lifeline Cell Technology (Frederick, MD) |
| Plasma protein fraction[18] | Alpha Therapeutics (Los Angeles, CA) |
| Epinephrine[19] | Sigma-Aldrich |
| Transferrin[20] | Sigma-Aldrich Life Technologies |
| Thyroxine 3 (T3)[21] | Sigma-Aldrich |
| Insulin[22] | Sigma-Aldrich |
| B27 supplement (50x)[23] | Life Technologies |

[1]EGM MV Microvascular Endothelial Cell Growth Medium contains growth factors, cytokines and supplements required for growth of endothelial cells.
[2]Airway Epithelial Cell Basal Medium contains essential and non-essential amino acids, vitamins, other organic compounds, trace minerals and inorganic salts required for growth of epithelial cells.
[3]DMEM is unique from other media as it contains 4 times the concentration of amino acids and vitamins than the original Eagle's Minimal Essential Medium.
[4]MEBM has been optimized for the growth of Mammary Epithelial cells in a serum-free environment.
[5]RPMI 1640 Medium was found suitable for growth of a variety of mammalian cells including AGS, Eso-1, HeLa, Jurkat, MCF-7, PC12, PBMC, astrocytes and carcinomas.
[6]Fibroblast Growth Medium was developed to support the growth of primary human fibroblasts.
[7]Hydrocortisone has been shown to enhance the ability of cells to synthesize extracellular matrix macromolecules.
[8]FGF stimulates the proliferation of a wide variety of cells including mesenchymal, neuroectodermal and endothelial cells.
[9]VEGF was found to yield higher endothelial cell proliferation in culture.
[10]R3-IGF-1 is mitogenic for a variety of cells including fibroblasts, osteoblasts, smooth muscle cells, fetal brain cells, neuroglial cells and erythroid progenitor cells; controls cell proliferation and differentiation; and regulates specific events in the G1 phase of the animal cell cycle.
[11]Ascorbic acid is an important water soluble antioxidant.
[12]EGF is a potent mitogenic factor for a variety of cultured cells of both ectodermal and mesodermal origin.
[13]Heparin supports the binding of Fibroblast Growth Factor (FGF) to its receptor and increases the stability of FGF.
[14]FBS is a serum-supplement for in vitro cell culture of eukaryotic cells.
[15]Penicillin/Streptomycin reduces the risk of contamination and is composed of 10,000 units/mL of Penicillin and 10,000 mg/mL of Streptomycin in saline solution.
[16]L-Alanyl-L-Glutamine is the dipeptide that enhances water uptake.
[17]Extract P is a cell supplement from Lifeline Cell Technology.
[18]Plasma protein fraction is composed of human albumin, alpha and beta globulins and not more than 1% gamma globulin.
[19]Epinephrine is an Adrenoceptor agonist.
[20]Transferrin physiologically provides iron to cells in culture.
[21]T3 is an iodine-containing hormone produced from thyroglobulin in the thyroid follicular cells. The stimulation of metabolic rate and regulation of growth and development by these hormones appear to be due to their effects on DNA transcription and, thus, protein synthesis.
[22]Insulin is used as a growth factor.
[23]The B-27 supplement is a stem cell, primary cell culture supplement.

The cell culture medium of this invention is a complete medium that supports the growth of endothelial cells, epithelial cells, fibroblasts and tumor cells. In one embodiment, the Microvascular Endothelial Cell Growth Medium; Airway Epithelial Basal Medium; DMEM, MEBM, or RPMI 1640; and Fibroblast Growth Medium are combined to prepare a basal medium, to which is added the remaining ingredients listed in Table 1. These additional ingredients may be added to freshly formulated basal medium, or they may be admixed in a solution of Dulbecco's Phosphate Buffered Saline (DPBS) and stored frozen, preferably at about −20° C. to about −70° C., until being added to basal medium to formulate the complete medium of this invention. The admixture may also be prepared as a 1×-1000× formulation, most preferably as a 1×, 100×, 500× or 1000× formulation, which is then diluted appropriately into basal culture medium to provide a 1× final formulation in the complete media.

The medium ingredients can be dissolved in a liquid carrier or maintained in dry form. If dissolved in a liquid carrier at the preferred concentrations shown in Table 2 (i.e., a "1× formulation"), the pH of the medium should be adjusted to about 7.0-7.6, preferably about 7.1-7.5, and most preferably about 7.2-7.4. The osmolarity of the medium should also be adjusted to about 275-350 mOsm, preferably about 285-325 mOsm, and most preferably about 280-310 mOsm. The type of liquid carrier and the method used to dissolve the ingredients into solution vary and can be determined by one of ordinary skill in the art with no more than routine experimentation. Typically, the medium ingredients can be added in any order.

The culture medium of this invention is typically sterilized to prevent unwanted contamination. Sterilization may be accomplished, for example, by filtration through a low protein-binding membrane filter of about 0.1-1.0 µm pore size (available commercially, for example, from Millipore, Bedford, Mass.) after admixing the concentrated ingredients to produce a sterile culture medium. Alternatively, concentrated subgroups of ingredients may be filter-sterilized and stored as sterile solutions. These sterile concentrates can then be mixed under aseptic conditions with a sterile diluent to produce a concentrated 1× sterile medium formulation. Autoclaving or other elevated temperature-based methods of sterilization are not favored, since many of the components of this culture media are heat labile and will be irreversibly degraded by temperatures such as those achieved during most heat sterilization methods.

The optimal concentrations for the medium ingredients are listed in Table 2. These ingredients can be combined to form the complete medium of this invention. As will be readily apparent to one of ordinary skill in the art, the concentration of a given ingredient can be increased or decreased beyond the specific amount disclosed and the effect of the increased or decreased concentration can be determined using only routine experimentation.

As described herein, the various normal cell types and tumor cells are cultured in the complete culture medium of this invention. By "culturing" or "culture" is meant the maintenance of cells in an artificial, in vitro environment. In general, the cells disclosed herein are cultured in a culture vessel, e.g., a glass, plastic, or metal container that can provide an aseptic environment for culturing cells. In particular embodiments, the method and kit of this invention employs the use of an ultra low attachment culture vessel. As is conventional in the art, an ultra low attachment surface is a covalently bonded hydrogel surface that is hydrophilic and neutrally charged. This surface minimizes cell attachment, protein absorption and enzyme activation thereby allowing cells to remain in a suspended, unattached state. Ultra low attachment culture vessels are known in the art and available from such sources as Corning (Lowell, Mass.).

The isolated cells can be plated according to the experimental conditions determined by the investigator. The examples herein demonstrate at least one functional set of culture conditions useful for cultivation of certain cells. It is to be understood, however, that the optimal plating and culture conditions for a given cancer cell type can be determined by one of ordinary skill in the art using only routine experimentation. For routine culture conditions, using this invention, cells can be plated onto the surface of culture vessels without attachment factors. The cell seeding densities for each experimental condition can be optimized for the specific culture conditions being used. For routine culture in plastic culture vessels, an initial seeding density of $1-5 \times 10^6$ cells per $cm^2$ is of particular use.

Cells of this invention are typically cultivated in a cell incubator at about 37° C. The incubator atmosphere should be humidified and should contain about 3-10% carbon dioxide in air, although cultivation of certain cell lines may require as much as 20% carbon dioxide in air for optimal results. Culture medium pH should be in the range of about 7.1-7.6, preferably about 7.1-7.4, and most preferably about 7.1-7.3.

In addition to the endothelial cells, epithelial cells, fibroblasts described above, the method and kit of this invention include an isolated cancer or tumor cell. The cancer cells of this invention can be primary cancer cells or cells of an established cancer cell line. Primary cancer cells can be isolated as described above and are of particular use in patient-specific therapeutic test systems (personalized medicine), wherein tumor cells are isolated from primary tissue biopsies, and grown in the Tumor in Dish perform. Primary cancers and cancer cell lines can be from urinary bladder cancer, prostate cancer, testicular cancer, ovarian cancer, breast cancer, cervical cancer, uterine cancer, lung cancer, esophageal cancer, laryngeal cancer, colon cancer, oral cancer, gastric cancer, stomach cancer, bladder cancer, head and neck squamous cell carcinoma, pancreatic cancer, kidney cancer, liver cancer, renal cancer, brain cancer, medulloblastoma, glioma, glioblastoma, thyroid cancer, melanoma, lymphoma, leukemia, multiple myeloma, mesothelioma, or metastatic cancer.

Cancer cell lines can be obtained from commercial sources including European Collection of Cell Cultures (ECCC, Salisbury UK), ATCC (Manassas, Va.), Coriell Institute for Medical Research (Camden, N.J.) Riken Bioresource Center (Japan) and the Japanese Collection of Research Bioresources (Japan). Examples of cancer cell lines of use in the kit and methods of this invention include, but are not limited to, non-small cell lung cancer cell lines NCI-H23 and NCI-H522, mesothelioma cell line NCI-H226, large cell lung cancer cell line NCI-H460, colorectal adenocarcinoma cell lines HT-29 and HCT-116, ovarian cancer cell lines OVCAR-3 and SK-OV-3, kidney cancer cell lines A-498 and Caki-1, melanoma cancer cell lines Malme-3M or SK-Mel-2, leukemia cell lines CCRF-CEM and K-562, myeloma cell line RPMI 8226, breast cancer cell lines MCF7 and MDA-MB-231, and prostate cancer cell lines DU-145 and PC-3.

Using the kit of this invention, a Tumor in Dish model can be prepared. In this respect, a method for preparing a Tumor in Dish model is provided. This method includes the steps of combining isolated human umbilical vein endothelial cells, isolated human lymphatic endothelial cells, isolated human fibroblast cells, isolated human epithelial cells and isolated cancer cells; and culturing the combination of cells in culture medium for a time sufficient to form a tumor. When the model is of a metastatic tumor, the isolated endothelial cells, fibroblast cells and epithelial cells can be cultured first (e.g., for 1 day to 1 week) and then the cancer cells are added. The time required for tumor development can be dependent upon a number of factors including the type of cancer and culture conditions, and can range from 1 day to 2-3 weeks.

The kit and method of this invention find application in the development of chemotherapies, radiotherapies, stem cell targeting therapies, antibody-based immunotherapies, and gene therapies, as well as basic research analyzing the biochemistry, morphology and pathophysiology of tumors including hypoxia, core necrosis, therapy resistance, exosomes, angiogenesis, invasion and metastasis. In addition, the Tumor in Dish model can be implanted in nude mice and the xenografts can be treated in vivo, to study the in vivo effect (pharmacokinetic/pharmacodynamic) of drugs. In this respect, the method of the invention can further include the steps of adding a test compound and determining whether the test compound inhibits, attenuates, prevents or reduces tumor growth, proliferation, size or metastasis.

The invention will be further described in the following examples, which do not limit the scope of the invention described in the claims.

Example 1

Establishment and Analysis of Tumor in Dish Model

To prepare the Tumor in Dish model, Human Umbilical Vein Endothelial Cells (HUVEC), Human Lymphatic endothelial cells (HLEC), Human lung fibroblast cells (MRC-5), and Human lung epithelial cells (NL20) were combined. To the normal cells was added human colon cancer cells (DLD1 stably expressing Green Fluorescent Protein ((GFP)). The cells were cultured on the medium composed of the ingredients listed in Table 2 in ultra low attachment plates.

TABLE 2

| Component | Amount |
| --- | --- |
| EGM MV Microvascular Endothelial Cell Growth Medium | 40% |
| Airway Epithelial Basal Medium | 20% |
| DMEM - Colosphere, Neurosphere or MEBM - Mammosphere or RPMI-1640 Medium - Esophageal and Gastric Cancer Spheres | 20% |
| Fibroblast Growth Medium | 20% |
| Hydrocortisone | 1.4 µg/ml |
| FGF6 | |
| VEGF | 2 ng/ml |
| R3-IGF-1 | 3 ng/ml |
| Ascorbic Acid | 20 µg/ml |
| hEGF | 6 ng/ml |
| Heparin calcium salt | 2.4 µg/ml |
| FBS | 1.2% |
| P/S | 0.6% |
| L-Alanyl-L-Glutamine | 0.48 mM |
| Extract P | 0.08% |
| Plasma protein fraction | 0.1% |
| Epinephrine | 0.2 µM |
| Transferrin | 1 µg/ml |
| T3 | 2 nM |
| Insulin | 1 µg/ml |
| B27 supplement (50x) | 2 ml/500 ml |

The particular growth factors and supplements used in this medium of the invention are sufficient to stimulate sphere formation. However, the medium is tailored for the particular cancer of interest. For example, when culturing colospheres or neurospheres, DMEM is employed. When culturing mammospheres, MEBM is used. When culturing esophageal or gastric cancer spheres, RPMI is used.

Figure 2:
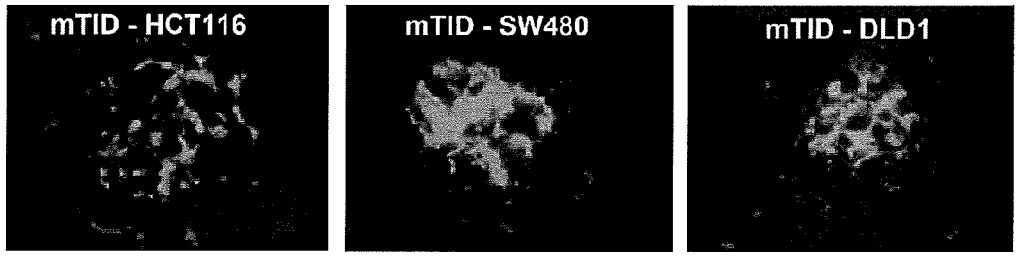
FIG. 2 shows the presence of a hypoxic core in the center of the TiD.

Live-dead staining of the TiD model indicated by the presence of colon cancer cells amongst numerous live cells (FIG. 1). Hematoxylin staining of the Tumor in Dish revealed the presence of different types of cells, with the necrotic cells in the central core mimicking the human tumor. Necrotic cells in the core of Tumor in Dish were observed when grown at a diameter of 200-600 µm. This was confirmed by staining the spheres, with a necrosis kit having fluorescent dye labeled 7-Amino-Actinomycin D (7-AAD), which specifically marks the necrotic cells that have lost membrane integrity. In addition, using a hypoxia probe, a hypoxic core was identified, which was similar to that observed in the human tumors suggesting that the TiD model exhibits characteristics similar to human tumors (FIG. 2).

Furthermore, proliferative cells, identified by expression of Ki67; drug resistant cells, identified by expression of P-glycoprotein (P-gp); and cancer stem cells identified by expression of DCLK1 and CD44, were shown to reside in the periphery of the Tumor in Dish. Conventional chemotherapy did not kill the tumor completely due to the presence of therapy resistant, quiescent cancer stem cells in the tumor. Therefore, targeting of the cancer stem cells can be studied in this Tumor in Dish model. Furthermore, penetrance of drugs into avascular tumors can also be analyzed when endothelial cells are omitted.

Scanning electron micrograph analysis of the Tumor in Dish model revealed the densely packed multicellular spheroid with micro vesicular structures on its surface and showed the presence of different types of cells as well as tube-like features.

Transmission electron micrograph analysis of the Tumor in Dish model provided additional information such as the presence of exosomes on the intracellular and extracellular surfaces of the cells in the sphere and a necrotic core in the center of the Tumor in Dish model.

Example 2

Exosome Analysis of Tumor in Dish Model

The Tumor in Dish model was exposed to a control and anti-cancer drug (compound 1). The media from the wells of control and drug-treated Tumor in Dish model were collected and exosomes were isolated using EXOQUICK exosome isolation kit (SBI, Mountain View, Calif.). RNA was isolated and real-time PCR analysis has conducted. This analysis indicated that the expression of DCLK1 and U6 mRNA decreased in the exosomes following compound 1 treatment. Exosomes are present in body fluids such as blood, milk, CSF, urine, etc. and have been shown to be released from the tumor to regulate tumor microenvironment. Therefore, regulation of tumor-released exosomes by anti-cancer agents can be analyzed using the Tumor in Dish model and system.

Example 3

Analysis of Anti-Cancer Drug in Tumor in Dish Model

Cells from control and anticancer drug B-treated Tumor in Dish model were dissociated into single cell suspension using trypsin and were FACS sorted to determine the effect of the drug on different types of cells. The results indicated that the number of GFP expressing DLD1 cells was measurably decreased in the drug-treated group, while the number of red florescence protein expressing normal fibroblast cells, purple color-labeled endothelial cells, and the blue color-labeled lung epithelial cells (pseudo colored) were moderately decreased by drug B. Immunofluorescence imaging studies confirmed that drug B significantly decreased the number GFP-DLD1 cells. In a similar study with compound 1, no significant decrease in DLD1-GFP cells was observed; however, there was a significant inhibition of endothelial cell growth, indicating inhibition of angiogenesis.

Figure 3A:
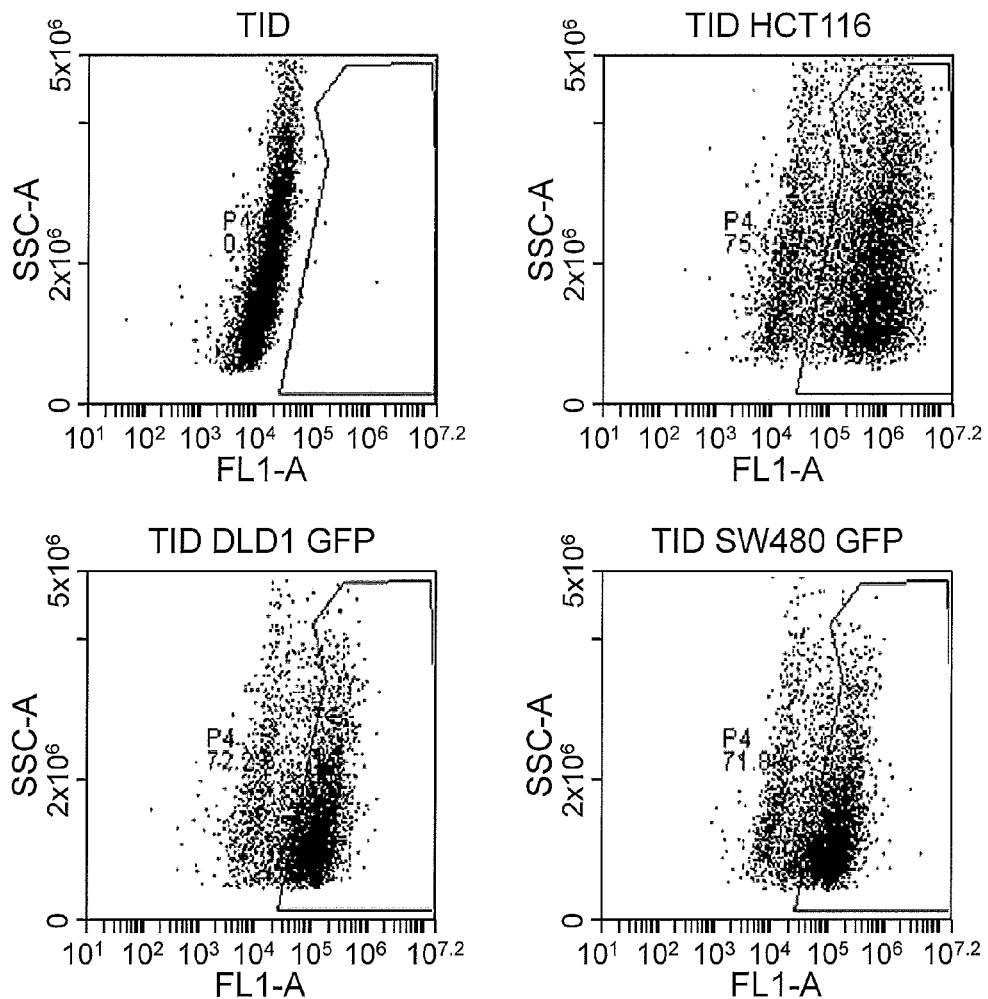
FIGS. 3A-3H show flow cytometry data sets from the TiD model with three colon cancer cell lines grown in the absence (FIG. 3A) or presence (FIGS. 3B-3G) of conventional colon cancer therapies. Colon cancer cell lines HCT116 (FIGS. 3B and 3C), SW480 (FIGS. 3D and 3E), and DLD1 (FIGS. 3F and 3G) were grown in the TiD model system and contacted with either 0.5, 5 or 25 µM Irinotecan (Iri) (FIGS. 3B, 3D, and 3F); 0.2, 2 or 10 µM SN38 (FIGS. 3B, 3D, and 3F); 0.5, 5 or 25 µM 5-fluorouracil (5FU) (FIGS. 3C, 3E and 3G); 0.5, 5 or 25 µM Oxaliplatin (Oxal) (FIGS. 3C, 3E and 34G).
Figure 3B:
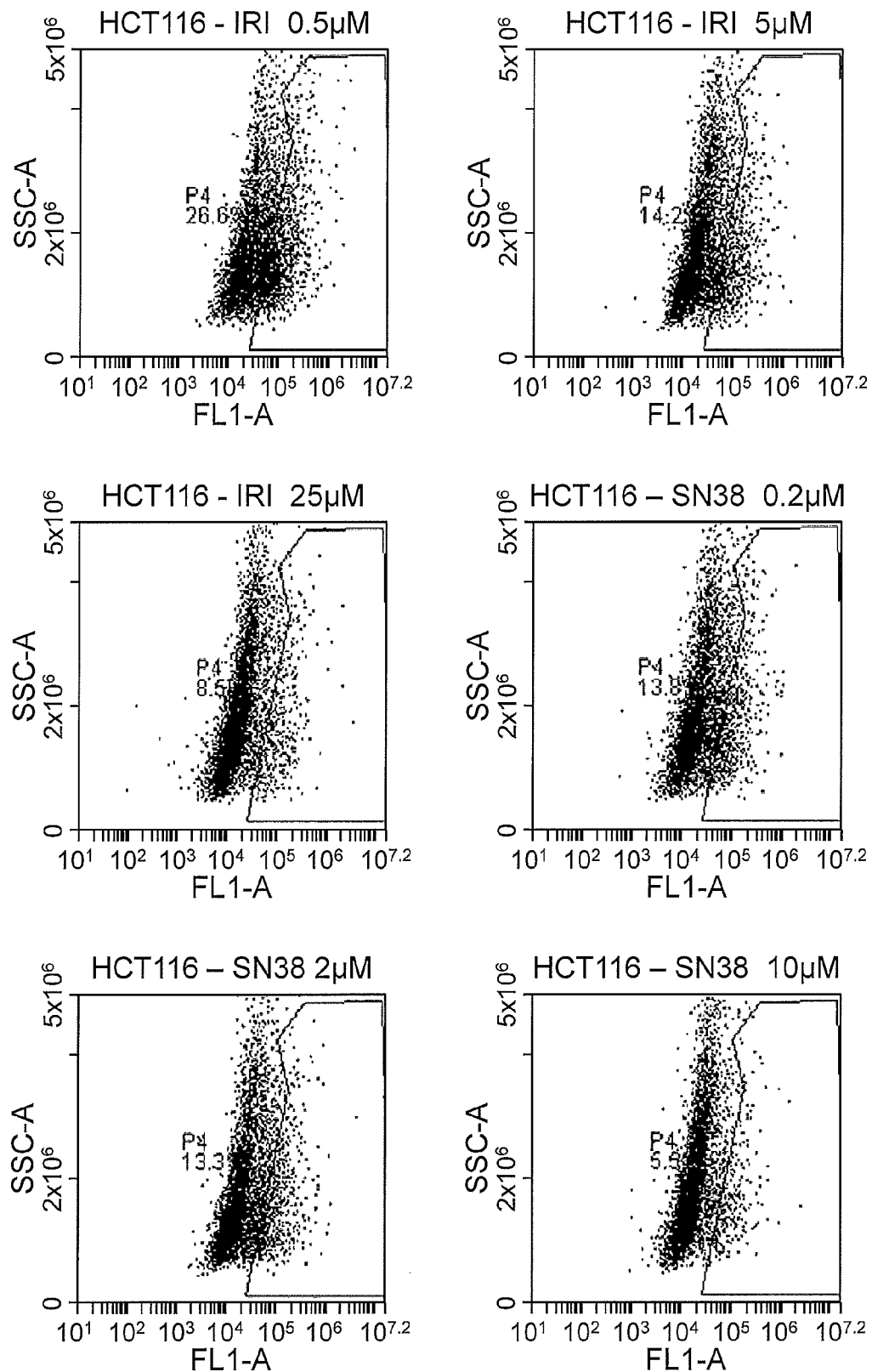
Figure 3C:
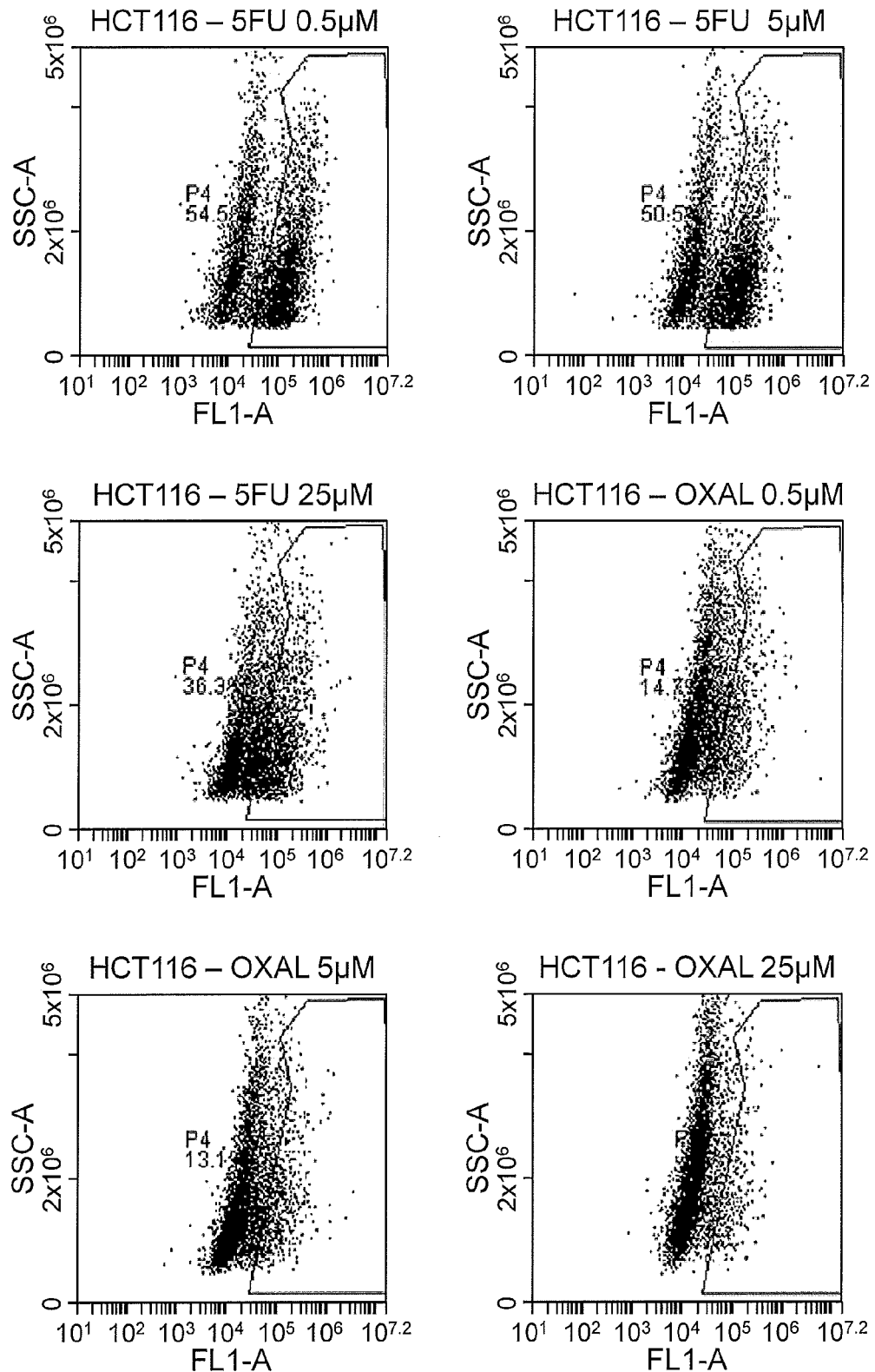
Figure 3D:
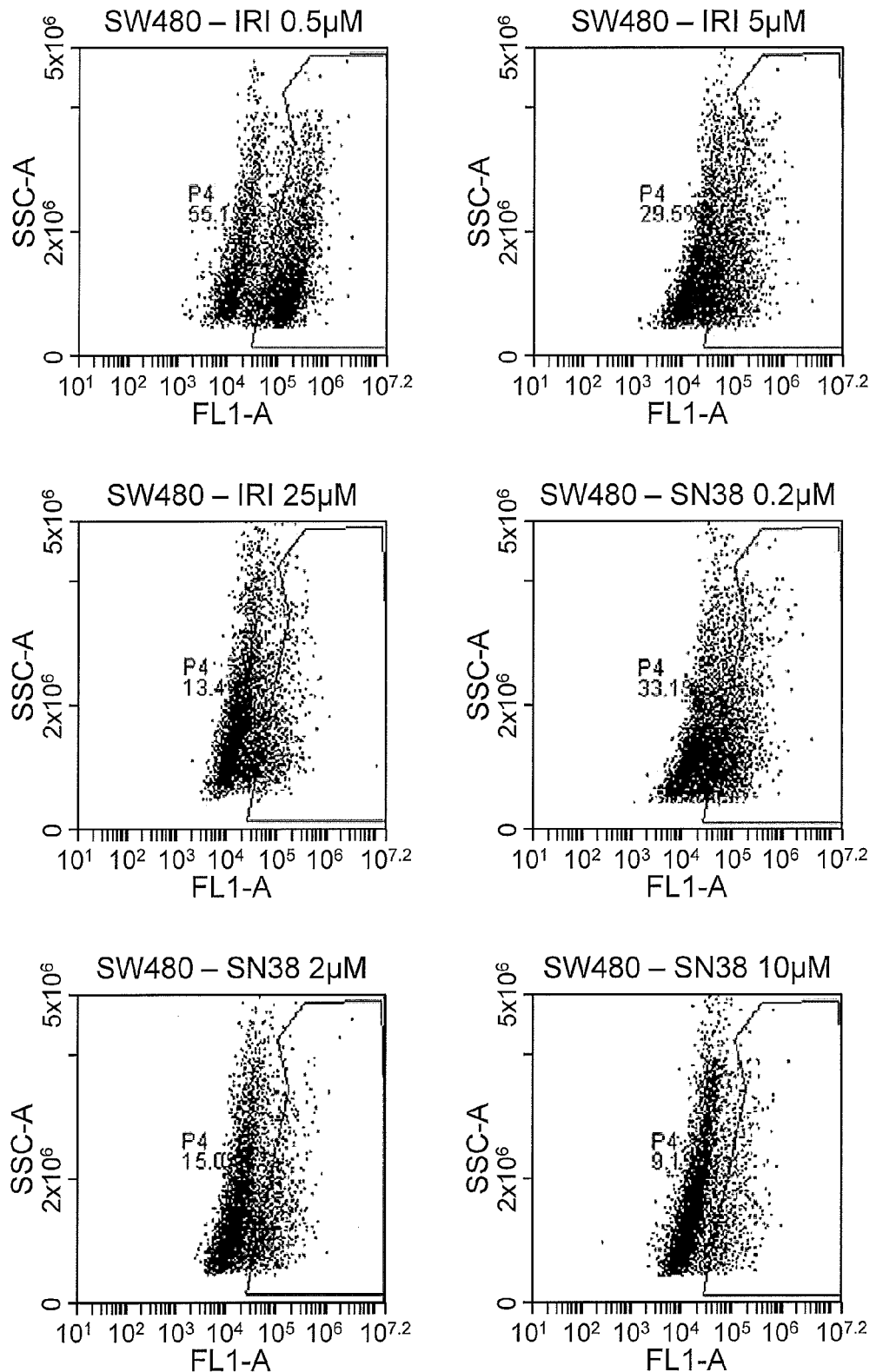
Figure 3E:
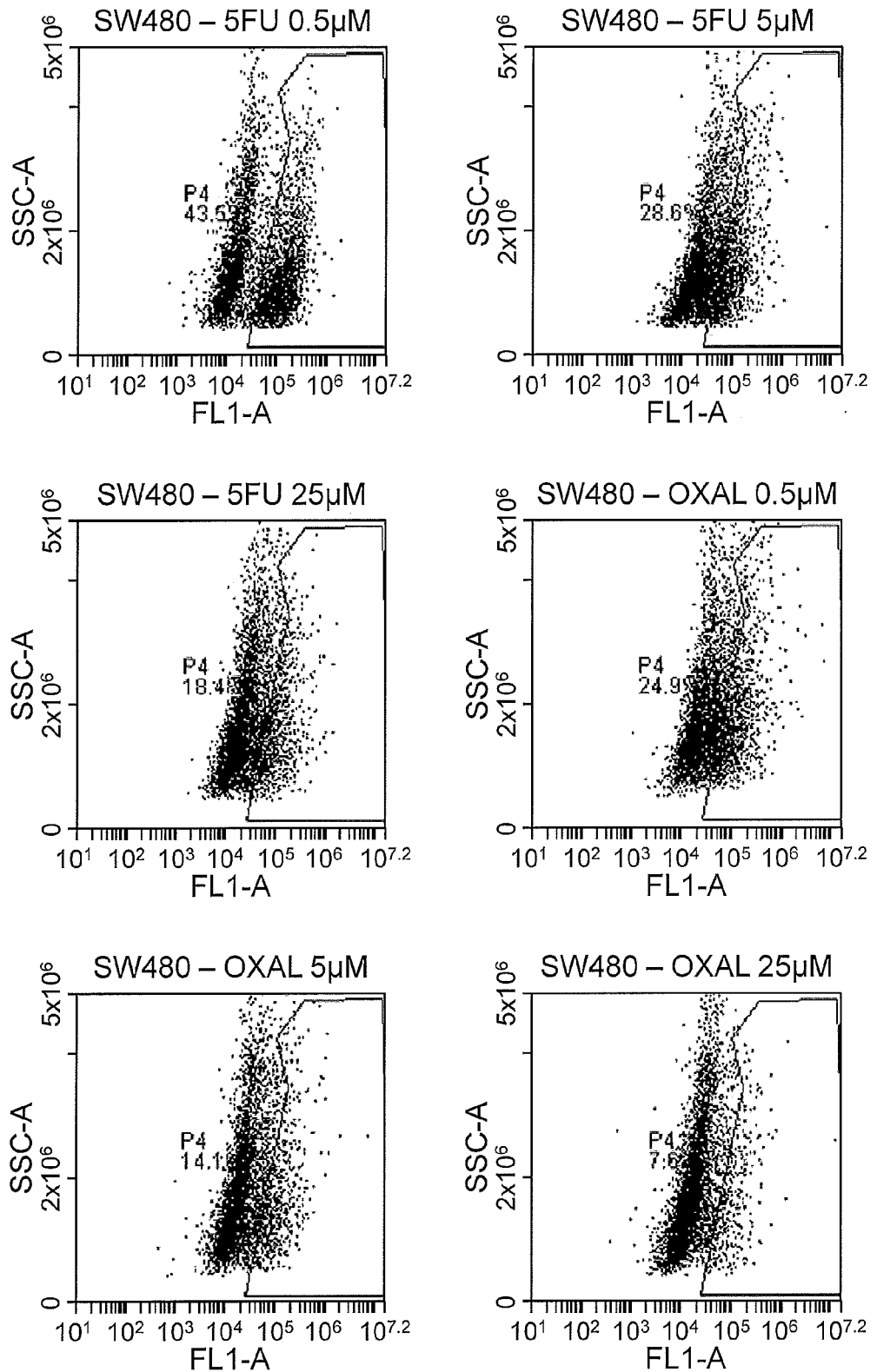
Figure 3F:
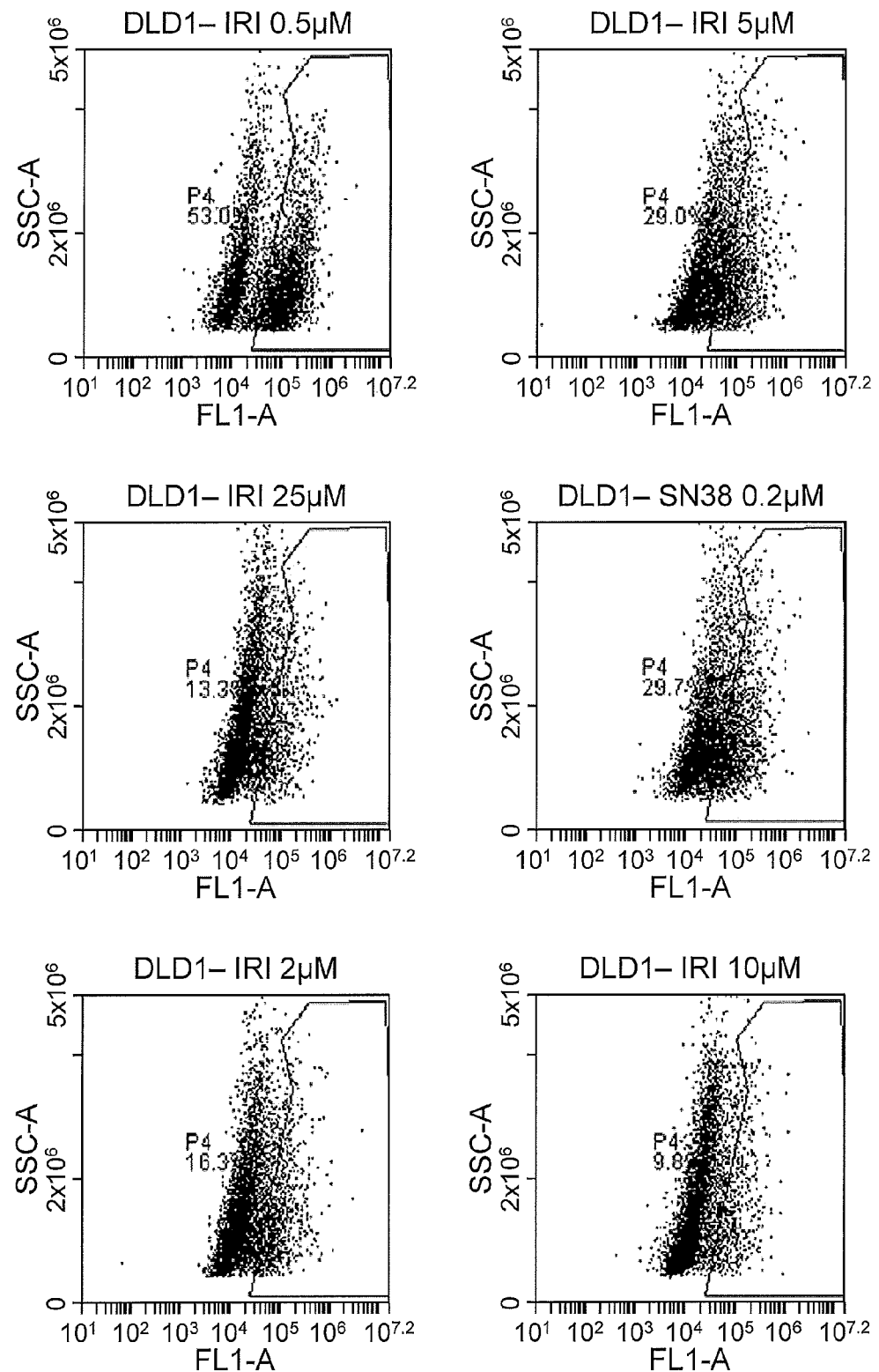
Figure 3G:
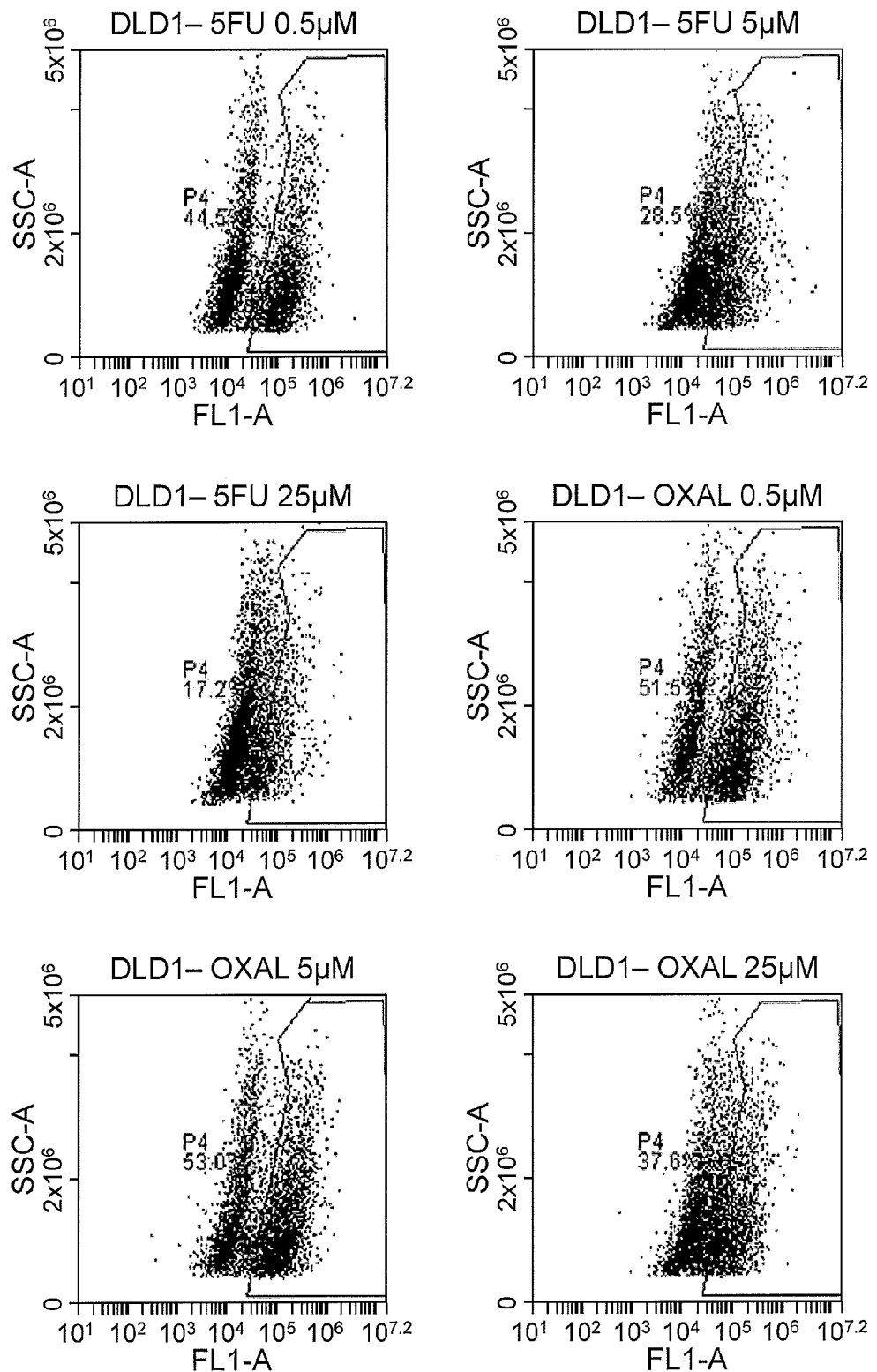
Figure 3H:
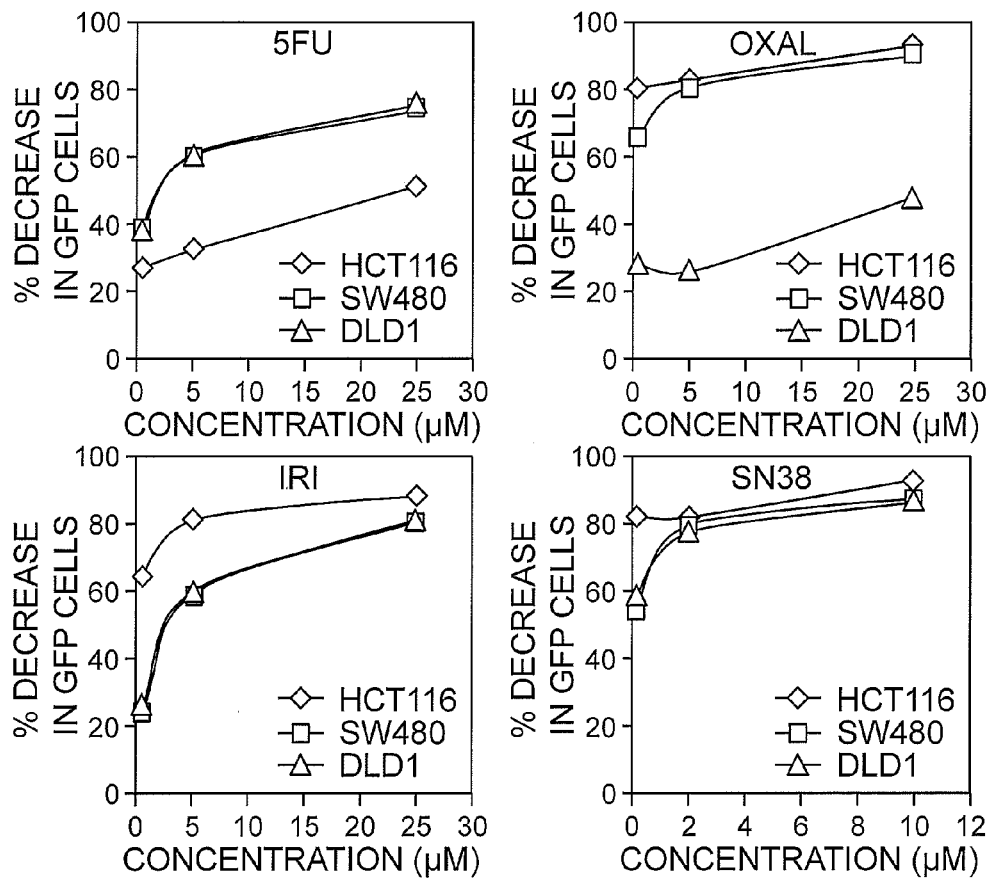

The effect of conventional anti-cancer agents were also tested in the TiD model using three different colon cancer cells lines HCT116, SW480, and DLD1. The three different cell lines were grown in the absence or presence of varying amounts of Irinotecan, SN38, 5FU or Oxaliplatin and subsequently analyzed by flow cytometry (FIG. 3A-3G). As illustrated in FIG. 3H, the results indicate that the TiD model can detect different responses to various drugs and is therefore of use in identifying appropriate drug and drug concentrations for patients in personalized medicine approaches to cure cancer.

Example 4

Lung Metastasis Model

Figure 4:
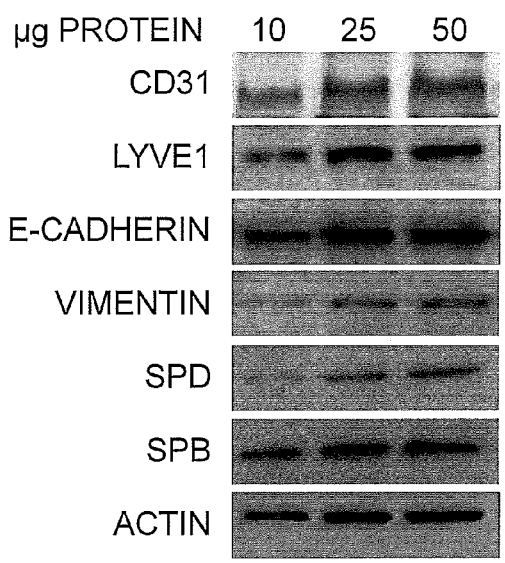
FIG. 4 shows a western blot of protein lysate of PLiD (Primitive lung in a Dish).

Using the same procedure described in Example 1, an in vitro colonization model for lung metastasis was developed. Four types of normal cells (NL20, MRC-5, HUVEC, and HLEC) were grown in a low attachment plate in the medium provided in Table 2. Western blot analysis of proteins expressed by the primitive lung in a dish (PLiD) clearly demonstrated the expression of Surfactant protein B and D, along with the specific markers of epithelial, mesenchymal, heme-endothelial and lymphatic endothelial cells (FIG. 4). These results demonstrate the ability to develop a primitive lung in a dish with all the cell types and forming semi-functional in vitro lung model for cancer research.

Accordingly, the PLiD model was prepared and, after three days of culture, GFP-DLD1 (colon cancer cells) were added to the normal cells. The results showed that after 12 hours, the DLD1 cells attached to the surface of the in vitro lung. On day 3 after adding the DLD1 cells to the normal cells, the DLD1 cells began to divide on the top of the in vitro lung, and on day 5 there was clear colonization of the cancer cells in the in vitro lung. Therefore, this model can be used to identify metastatic inhibitors with low toxicity to normal cells.

The Tumor in Dish model containing normal lung epithelial, fibroblast cells, normal lymphatic endothelial along with DLD1-GFP colon cancer cells and HUVEC-mCherry endothelial cells were nuclear stained with DAPI-blue and 3D fluorescence images were captured using IN CELL 6000 (NIH). The results clearly showed the presence of lumen formation and electron microscopy revealed the structure of exosomes. This in vitro lung model was fixed and processed for transmission electron microscopic analysis and the representative image showed the presence of the surfactant ultrastructure. The immunohistochemical analysis of the section of Tumor in Dish stained for ALDH1 (stem cell marker) revealed the presence of numerically rare cancer stem cells in the periphery of the sphere.

Therefore, the Tumor in Dish model can be used in a method to identify compounds that inhibit cancer invasion and/or migration. Such a method would involve placing the Tumor in Dish model on top of collagen with and without compounds and monitoring invasion and/or migration. In addition to invasion and migration, the Tumor in Dish model can be used to monitor tumor dissociation by drugs. Furthermore, the functional aspects of the normal cells in the Tumor in Dish and the effect of drugs on their function also can be studied. In this respect, hypoxia and its effect on cancer cells, cancer stem cells and the surrounding normal cells can be delineated using this model.

Example 5

Tumor in Dish Model Using Primary Tumor Cells

Figure 5:
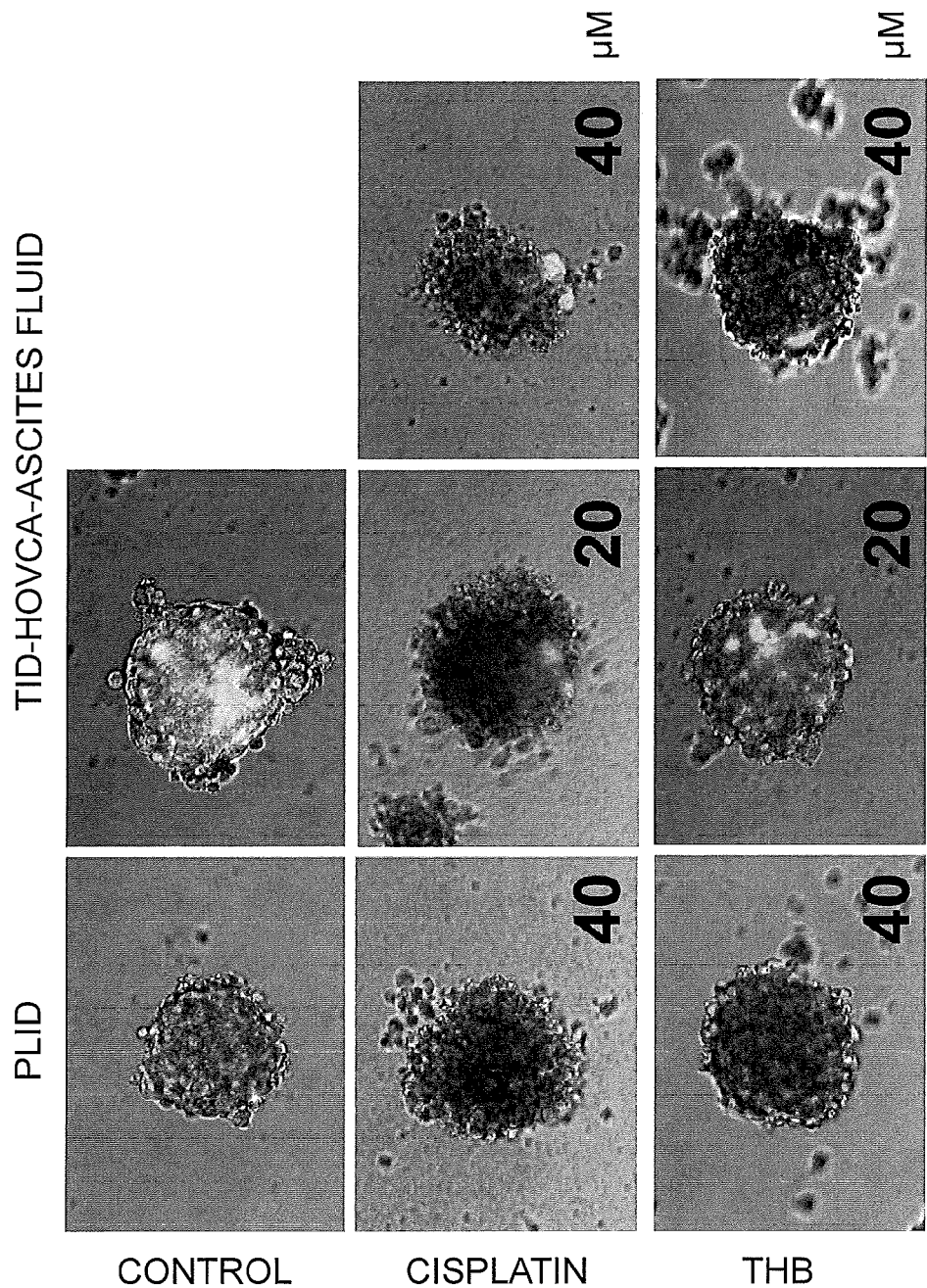
FIG. 5 shows human ovarian cancer (hOvCa) epithelial cells isolated from the ascites fluid of a patient and combined with cells to form a TiD.

Human ovarian cancer epithelial cells were isolated from the ascites fluid of a patient and combined with normal cells as described in Example 1 to form TiD. As shown in FIG. 5, the TiD model could be used to grow human primary tumor samples. Furthermore, treatment with cisplatin affected the normal cells in the PLiD, but killed most of the ovarian cancer cells from the ascites fluid. Interestingly, this TiD model can also give additional information about the effect of the drugs on the surrounding normal cells. For example, it is evident from the analysis presented in FIG. 5 that THB, an analog of a natural phytochemical (marmelin), killed most of the cancer cells better than cisplatin and had less toxic effects on the normal cells.

Example 6

Brain Tumor Models

Using the same procedure described in Example 1, TiD models were prepared using the medulloblastoma cell line DaoY (FIG. 6A) and glioblastoma cell line U251 (FIG. 6B). The cells were treated with 5FU, doxorubicin or Honokiol to determine effects on growth. The results of this analysis indicate that these TiD models are of use in determining efficacy and toxicity of compounds against brain tumor cells.

Example 7

Efficacy of Anti-VEGF Antibody in TiD Model

Figure 7A:
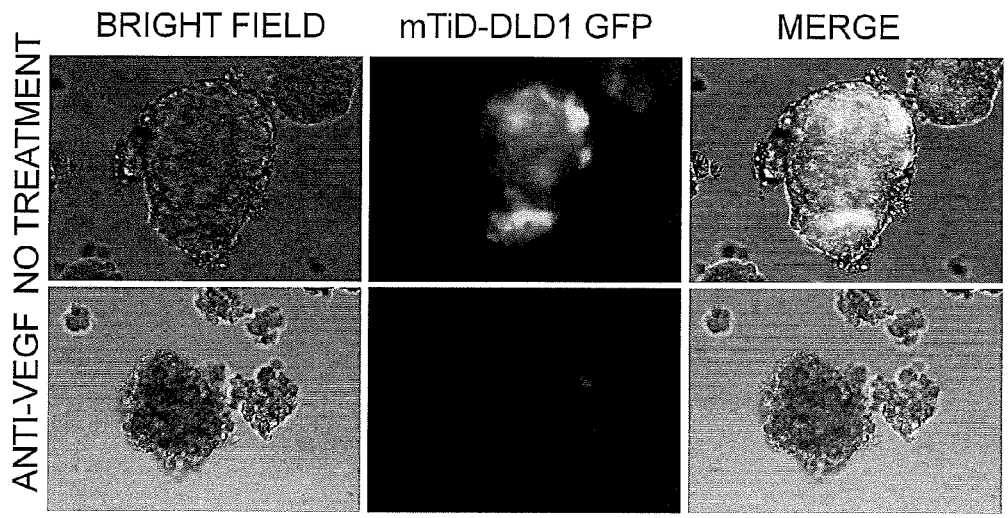
FIGS. 7A and 7B demonstrate the utility of the TiD model for studying the effect of anti-VEGF antibody in DLD1 (FIG. 7A) and HCT116 (FIG. 7B) colon cancer cells.
Figure 7B:
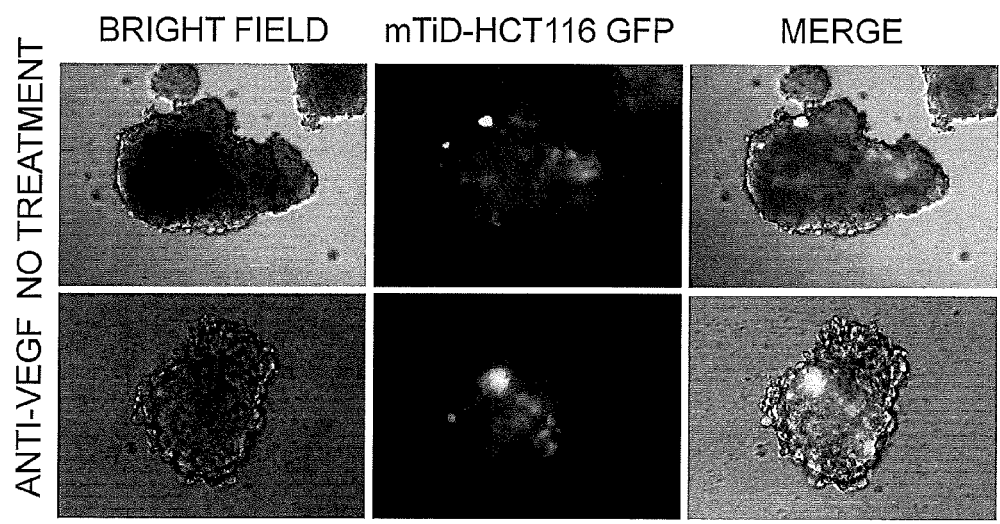

VEGF-targeted agents such as the anti-VEGF monoclonal antibody has been shown to provide clinical benefit in patients with primary (colon, breast) and metastatic cancers. To test of effects of anti-VEGF therapy in the TiD model, colon cancer cells were prepared using the procedure described in Example 1 and contacted with anti-VEGF antibody. The results presented in both FIGS. 7A-7B clearly show that anti-VEGF therapy is effective only in DLD1 colon cancer cells (FIG. 7A), while there were minimal efficacy of anti-VEGF against HCT116 colon cancer cells (FIG. 7B). This indicates that TiD model can be helpful in determining the clinical efficacies of drugs that are under development and in the clinical trials. Again, TiD model is highlighting the importance of personalized therapy for cancer patients.

What is claimed is:

1. A method for preparing a Tumor in Dish model comprising
   (a) combining normal cells consisting of isolated human umbilical vein endothelial cells, isolated human lymphatic endothelial cells, isolated human fibroblast cells, and isolated human epithelial cells and with isolated cancer cells; and
   (b) culturing the combination of cells in culture medium for a time sufficient to form a tumor thereby preparing a Tumor in Dish model, wherein the culture medium consists of Microvascular Endothelial Cell Growth Medium; Airway Epithelial Basal Medium; Dulbecco's Modified Eagle's Medium, Mammary Epithelial Cell Basal Medium, or Roswell Park Memorial Institute 1640 Medium; Fibroblast Growth Medium; Hydrocortisone; Fibroblast growth factor 6; R3-Insulin-Like Growth Factor-I; Ascorbic Acid; Vascular Endothelial Growth Factor; Human Epidermal Growth Factor; Heparin; Fetal Bovine Serum; Antibiotics; L-Alanyl-L-Glutamine; Extract P; Plasma Protein Fraction; Epinephrine; Transferrin; Thyroxine 3; Insulin; and B27 supplement; wherein there are no other culture medium ingredients added during the time sufficient to form a tumor.

2. The method of claim 1, wherein the tumor comprises colon cancer, lung metastasis, ovarian cancer, medulloblastoma or glioblastoma.

3. The method of claim 1, wherein step (a) comprises
   (i) combining normal cells consisting of isolated human umbilical vein endothelial cells, isolated human lymphatic endothelial cells, isolated human fibroblast cells and isolated human epithelial cells;
   (ii) culturing the combination of normal cells of (i);
   (iii) adding isolated cancer cells to the cultured normal cells of (ii).

4. The method of claim 1, wherein the step of culturing the normal cells is carried out in an ultra low attachment culture vessel.

5. The method of claim 1, further comprising the steps of:
   (c) adding a test compound; and
   (d) determining whether the test compound inhibits, attenuates, prevents or reduces tumor growth, proliferation, size or metastasis.

* * * * *